US006878535B2

(12) United States Patent
Yaguchi et al.

(10) Patent No.: US 6,878,535 B2
(45) Date of Patent: Apr. 12, 2005

(54) PROCESS FOR PRODUCING SOYASAPOGENOL B AND NOVEL MICROORGANISMS

(75) Inventors: Takashi Yaguchi, Yokohama (JP); Goh Tsujiuchi, Yokohama (JP); Nobuaki Kushida, Yokohama (JP); Masato Tani, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 183 days.

(21) Appl. No.: 10/258,539

(22) PCT Filed: Apr. 25, 2001

(86) PCT No.: PCT/JP01/03571

§ 371 (c)(1),
(2), (4) Date: Nov. 19, 2002

(87) PCT Pub. No.: WO01/81612

PCT Pub. Date: Nov. 1, 2001

(65) Prior Publication Data

US 2004/0029214 A1 Feb. 12, 2004

(30) Foreign Application Priority Data

Apr. 25, 2000 (JP) ....................................... 2000-123924

(51) Int. Cl.[7] .............................. C12P 7/02; C12P 1/00; C12P 33/00; C12P 7/58

(52) U.S. Cl. ........................... 435/155; 435/41; 435/52; 435/137

(58) Field of Search ............................ 435/41, 52, 137, 435/155

(56) References Cited

FOREIGN PATENT DOCUMENTS

| | | |
|---|---|---|
| JP | 61-037749 | 2/1986 |
| JP | 10-234396 | 9/1998 |

*Primary Examiner*—Ralph Gitomer
*Assistant Examiner*—Kailash C. Srivastava
(74) *Attorney, Agent, or Firm*—Wenderoth, Lind & Ponack, L.L.P.

(57) ABSTRACT

An objective of the present invention is to provide a method of producing soyasapogenol B and to provide novel microorganisms. The present invention provides a method of producing soyasapogenol B comprising the steps of culturing microorganisms that belong to genus *Neocosmospora* or genus *Eupenicillium*, in a medium containing a glycoside having soyasapogenol B as an aglycone, and then collecting soyasapogenol B from the resulting culture.

14 Claims, No Drawings

PROCESS FOR PRODUCING SOYASAPOGENOL B AND NOVEL MICROORGANISMS

This application is a 371 of PCT/JP01/03571, filed Apr. 25, 2001, which claims priority to Japanese application Serial No. 2000-123924, filed Apr. 25, 2000.

BACKGROUND OF THE INVENTION

1. Field of the Invention

The present invention relates to a method of producing soyasapogenol B using a microbial culture, and to a novel strain which belongs to genus *Neocosmospora* and a novel strain which belongs to genus *Eupenicillium.*

2. Background Art

Soyasapogenol B is one of the aglycones of saponins contained in legumes and was first isolated from soybean seeds (Glycine max MERRILL, seeds) and its structure has been determined (Chem. Pharm. Bull. 24: 121–129, 1976, Chem. Pharm. Bull. 30: 2294–2297, 1982). Glycosides (e.g., soyasaponin) having soyasapogenol B as an aglycone have been reported to have various physiological activities, such as antioxidation effect, hepatoprotective effect, serum lipid improving effect, platelet aggregation suppressing effect, and anticomplementary activity, and their potential use as preventive and therapeutic drugs for immune diseases, such as nephritis, rheumatism and systemic lupus erythematosus, autoimmune diseases, and thrombosis is indicated (Kagaku to Seibutsu 21:224–232, 1983; Japanese Patent Laid-open Publication No.37749/1986). Further, as for soyasapogenol B, anticomplementary activity, platelet aggregation suppressing effect, and growth suppressing effect on cells derived from human colon cancer and human ovarian cancer have been reported (Japanese Patent Laid-open Publication No.37749/1986; Japanese Patent Laid-open Publication No.234396/1998).

Soyasapogenol B can be obtained, for example, by chemically hydrolyzing sugar chains of soyasaponins I–V contained in soybean seeds. However, this is not an effective production method because a considerable number of by-products are produced under the conditions for acid hydrolysis or the like. Furthermore, when a crude extract derived from soybeans is used as the material for the chemical hydrolysis, aglycones other than soyasapogenol B are produced at the same time because this crude extract contains soyasaponins $A_1$–$A_6$ or the like, other than soyasaponins I–V, which complicates the purification process and causes other problems.

On the other hand, as for methods of producing soyasapogenol B using microorganisms, a method with genus *Streptomyces* (Chem. Pharm. Bull. 32: 1287–1293, 1984) and a method with genus *Penicillium* (Japanese Patent Laid-open Publication No. 234396/1998) are known. However, these methods of producing soyasapogenol B are not sufficient for productivity and practicality. Further, it has been reported that soyasapogenol B is produced as a by-product when an acidic oligosaccharide having glucuronic acid as the reducing end terminal is produced upon hydrolyzing a glucuronide saponinusing the enzyme (glucuronidase) produced by microorganisms that belong to genus *Aspergillus* or a culture containing this enzyme (Japanese Patent Publication No. 32714/1995). However, this method is primarily a method of producing acidic oligosuccharides, and only a qualitative confirmation of soyasapogenol B is described.

As mentioned above, soyasapogenol B has various physiological activities wherein its use as a pharmaceutical or health food, or as a material for derivatives of further improved usefulness can be expected. Accordingly, there are needs to develop more efficient and less costly methods of producing soyasapogenol B.

SUMMARY OF THE INVENTION

An objective of the present invention is to provide an efficient method of producing soyasapogenol B.

Another object of the present invention is to provide novel microorganisms which can efficiently convert a glycoside to soyasapogenol B.

The present inventors have now found microorganisms which selectively hydrolyze a glycoside having soyasapogenol B as an aglycone, such as soybean saponin, and efficiently convert it to soyasapogenol B. The present inventors have also found that these microorganisms are novel strains that belong to genus *Neocosmospora* and genus *Eupenicillium.*

A method of producing soyasapogenol B according to the present invention is a method which comprises the steps of culturing microorganisms that belong to genus *Neocosmospora* and convert a glycoside having soyasapogenol B as an aglycone to soyasapogenol B, in a medium containing a glycoside having soyasapogenol B as an aglycone, and then collecting soyasapogenol B from the resulting culture.

A method of producing soyasapogenol B according to the present invention is a method which comprises the steps of culturing microorganisms that belong to genus *Eupenicillium* and convert a glycoside having soyasapogenol B as an aglycone to soyasapogenol B, in a medium containing a glycoside having soyasapogenol B as an aglycone, and then collecting soyasapogenol B from the resulting culture.

Furthermore, a method of producing soyasapogenol B according to the present invention is a method which comprises the steps of bringing a glycoside having soyasapogenol B as an aglycone into contact with a culture which is obtained by culturing microorganisms that belong to genus *Neocosmospora* and convert a glycoside having soyasapogenol B as an aglycone to soyasapogenol B, and then collecting soyasapogenol B from the resulting culture.

A method of producing soyasapogenol B according to the present invention is a method which comprises the steps of bringing a glycoside having soyasapogenol B as an aglycone into contact with a culture which is obtained by culturing microorganisms that belong to genus *Eupenicillium* and convert a glycoside having soyasapogenol B as an aglycone to soyasapogenol B, and then collecting soyasapogenol B from the resulting culture.

Novel strains according to the present invention are *Neocosmospora vasinfecta* var. *vasinfecta* PF1225 (FERM BP-7475) and mutants thereof.

Furthermore, novel strains according to the present invention are *Eupenicillium brefeldianum* PF1226 (FERM BP-7476) and mutants thereof.

A microorganism which belongs to genus *Neocosmospora* can be *Neocosmospora vasinfecta* var. *vasinfecta*, more preferably *Neocosmospora vasinfecta* var. *vasinfecta* PF1225 (FERM BP-7475).

A microorganism which belongs to genus *Eupenicillium* can be *Eupenicillium brefeldianum*, more preferably *Eupenicillium brefeldianum* PF1226 (FERM BP-7476).

DETAILED DESCRIPTION OF THE INVENTION

1. Mycological Characteristics of Strain PF1225

(1) Characteristics of Colonies

Colonies growing on oatmeal agar at 25° C. attained a diameter of more than 85 mm in 14 days, and were light grayish brown, floccose and plane. Dark orange ascomata were produced at a center of colonies. The reverse sides of the colonies were grayish brown.

Colonies growing on Czapek yeast extract agar at 25° C. attained a diameter of 80 mm in 14 days, and were light brown, floccose, and radially sulcate. Ascomata were produced in an aerial hypare. The reverse sides of the colonies were yellow brown.

At 37° C., the growth was restrictedly, and ascoma was not produced.

(2) Morphological Characteristics

Ascomata were superficial, ostiolate, globose to ovoid and 300–450×250–350 μm. Peridium were membranceous and consisting of texture angularis with cells measuring 10–25 μm in diam. Asci were 8-spored, cylindrical, short-stipitate, uniseriately, 75–100×10–12 μm and evanescent at maturity. Ascospores were globose to subglobose, or muriform, rugose and 12–14×9–11 μm.

Phialides were produced on sides of hyphae and 25–50×2.5–3 μm. Conidia were ellipsoidal to cylindrical, straight, more or less curved, smooth-walled, 5–12.5×2.5–3 μm, born mucosely.

The above characteristics of strain PF1225 indicate that this fungus belongs to *Neocosmospora vasinfecta* var. *vasinfecta*. Taxonomic studies of the strain were done according to the method of Cannon ("A Revision of The Genus *Neocosmospora*" P. F. Cannon, D. L. Hawksworth. Trans. Br. Mycol. Soc. 84(4) 673–688 (1984)).

Strain PF1225 was deposited at the National Institute of Bioscience and Human-Technology, the National Institute of Advanced Industrial Science and Technology (1–3, Higashi 1-Chome, Tsukuba City, Ibaraki, Japan), dated Mar. 13, 2000. The accession number is FERM BP-7475.

2. Mycological Characteristics of Strain PF1226

(1) Characteristics of Colonies

Colonies growing on Czapek yeast extract agar at 25° C. attained a diameter of more than 85 mm in 14 days, and were light grayish brown, velvety and radially sulcate. Ascomata were produced scattered on the agar surface. The reverse sides of the colonies were yellowish brown.

Colonies growing on malt extract agar at 25° C. attained a diameter of 80 mm in 14 days, and were white to light brown, velvety to floccose, and plane. Ascomata were conspicunose. The reverse sides of the colonies were yellow brown.

Colonies growing on oatmeal agar at 25° C. attained a diameter of more than 85 mm in 14 days, and were light brown, velvety and plane. Ascomata were produced abundantly on the agar surface. Hyaline and clear exudete was produced. The reverse sides of the colonies were yellowish brown.

At 37° C., the growth was restrectely.

(2) Morphological Characteristics

Ascomata were superficial, non-ostiolate, globose to ovoid and 100–300 μm in diam. Peridium were membranceous and consisting of texture angularis with cells measuring 10–25 μm in diam. Asci were 8-spored, ellipsoidal to pyriform, born singly, 10–12.5×7.5–10 μm and evanescent at maturity. Ascospores were globose to subglobose, spinulose and 2.5–3×2–2.5 μm.

Stipes of conidiophores were born on side of hypare, smooth-walled, 25–150×2–2.5 μm. Penicilli were monoverticillate. Phialides were ampulliform, 7.5–12.5×2–2.5 μm and 3–6 per stipe. Conidia were globose to subglobose, smooth-walled, 2–2.5 μm, born in chains.

The above characteristics of strain PF1226 indicate that this fungus belongs to *Eupenicillium brefeldianum*. Taxonomic studies of the strain were done according to the method of Pitt ("The Genus *Penicillium* and its teleomorphic states *Eupenicillium* and Talaromyces" John I. Pitt. Academic Press (1979)).

Strain PF1226 was deposited at the National Institute of Bioscience and Human-Technology, the National Institute of Advanced Industrial Science and Technology (1–3, Higashi 1-Chome, Tsukuba City, Ibaraki, Japan), dated Mar. 3, 2000. The accession number is FERM BP-7476.

Characteristics of strains PF1225 and PF1226 are variable as seen with other microorganisms. For example, any microorganism which produces soyasapogenol B by hydrolyzing a glycoside having soyasapogenol B as an aglycone, including mutant strains (naturally occurring or induced), plasmozygotes or genetic recombinants, derived from strains PF1225 and PF1226, can be used for a method of producing soyasapogenol B according to the present invention.

3. Culture of Strains PF 1225 and PF 1226

In a method of production according to the present invention, microorganisms that belong to genus *Neocosmospora*, such as strain PF1225, or microorganisms that belong to genus *Eupenicillium*, such as PF1226, can be cultured in a medium containing nutrients utilizable by ordinary microorganisms, supplemented with a substance containing a glycoside having soyasapogenol B as an aglycone.

Known glycosides having soyasapogenol B as an aglycone include soyasaponins I, II, III, IV, and V, azukisaponins II and V, astragaloside VIII, and sophoraflavoside I, which are primarily found in legumes. These glycosides can be added directly to a medium. More practical methods include a method in which a substance extracted from legumes containing these glycosides, such as soybeans (Glycine max MERRILL), azuki beans (*Vigna angularis* (WILLD.) OHWI et OHASHI), astragali radix (*Astragalus membranaceus* BUNGE), sophorae radix (*Sophora flavescens* AITON), and alfalfa (*Medicago sativa* L.), using hot water, alcohol or aqueous alcohol, is added, and a method in which the target substance appropriately removed impurities from these extracts to increase the content of the glycoside having soyasapogenol B as an aglycone is added. Examples of a substance containing a glycoside having soyasapogenol B as an aglycone include a substance extracted from soybeans or defatted soybeans (soybean cake) by hot water, alcohol or aqueous alcohol, or preferably a substance from which impurities such as proteins, sugars and lipids are removed by an ordinary method.

Nutrients conventionally known and used for fungus culture are used as nutrient sources. For example, glucose, sucrose, starch syrup, dextrin, starch, glycerol, molasses, and animal and vegetable oils can be used as a carbon source. Soybean powder, wheat germ, cornsteep liquor, cottonseed grounds, meat extract, peptone, yeast extract, ammonium sulfate, sodium nitrate, urea, and the like can be used as a nitrogen source. If necessary, inorganic salts which can produce sodium, potassium, calcium, magnesium, cobalt, chloride, phosphate, sulfate and other ions can be added effectively. Further, organic and inorganic substances which can enhance microbial conversion of soyasapogenol B from a glycoside having soyasapogenol B as an aglycone can be appropriately added.

The most suitable culture method is a culture under an aerobic condition, in particular a shake culture. An appropriate culture temperature is between 25° C. and 30° C., but in most cases, the culture is carried out at about 26° C. The accumulation of produced soyasapogenol B reaches its maximum generally in 2 to 14 days in any of a static culture, shake culture and tank culture, depending on the medium and culture conditions used. Culturing is stopped when the accumulation of soyasapogenol B in the culture reaches the maximum, and then the target substance is isolated and purified from the culture.

4. Purification of Soyasapogenol B

Soyasapogenol B thus produced can be isolated and purified from the culture depending on its characteristics. Namely, it can be purified by a solvent extraction method using an organic solvent, an absorption-desorption method using an absorbent, a molecular partition method using a gel filtration agent, a precipitation method, a recrystallization method, or the like, alone or in combination as appropriate. For example, extraction from a culture containing soyasapogenol B is carried out using ethyl acetate, and the resulting organic solvent layer can be concentrated under reduced pressure. The resultant concentrate is adsorbed on a silica gel column, and then chromatographed using a mixed solvent system with chloroform-methanol, hexane-ethyl acetate, or hexane-acetone. Further, if necessary, soyasapogenol B can be purified using a gel filtration agent such as Sephadex LH-20 (a product of Pharmacia Fine Chemicals). Further, soyasapogenol B can be crystallized from an organic solvent such as ethyl acetate or methanol.

EXAMPLES

The present invention will be explained more in detail referring to examples; however, the present invention is not restricted to these examples. Namely, a method of producing soyasapogenol B can be modified in various ways based on the strains to be used for microbial conversion and the characteristics of soyasapogenol B, and those modified methods are also within the scope of the method of the production according to the present invention.

Example 1

Production of Soyasapogenol B by Strain PF1225

A medium containing 2.0% starch, 1.0% glucose, 0.5% polypeptone, 0.6% wheat germ, 0.3% yeast extract, 0.2% soybean grounds and 0.2% calcium carbonate (pH 7.0 before sterilization) was used as a seed medium.

A medium containing 4.0% malt extract, 2.0% yeast extract, 0.2% potassium dihydrogenphosphate, 0.2% ammonium sulfate, 0.03% magnesium sulfate (heptahydrate), 0.03% calcium chloride (dihydrate), supplemented with 1.0% soybean saponin (a product of Koshiro Seiyaku), was used as a production medium.

The above-mentioned seed medium (20 ml) dispensed into a 100-ml Erlenmeyer flask was sterilized at 120° C. for 15 minutes. One platinum loopful of slant agar culture of PF1225 strain (FERM BP-7475) was inoculated into the medium thus prepared and incubated at 25° C. for 2 days with shaking. Next, the production medium (100 ml) dispensed into a 500-ml Erlenmeyer flask was sterilized at 120° C. for 15 minutes, into which 2 ml of the culture thus obtained were inoculated and incubated at 25° C. for 4 days with shaking.

The resulting culture (300 ml) was extracted with ethyl acetate (300 ml) and the ethyl acetate layer was concentrated under reduced pressure to obtain an oily substance (750 mg). This substance was applied to a column of silica gel (Wako Gel C-300, a product of Wako Pure Chemicals; 70 g) and eluted with hexane-acetone (3:1). Fractions each containing a single substance were collected and concentrated to dryness to obtain soyasapogenol B (150 mg) and soyasapogenol A (8 mg).

Thin layer chromatography (TLC: MERCK 1.05715.; development system: hexane-acetone (2:1))

Soyasapogenol B: Rf 0.38
Soyasapogenol A: Rf 0.28

Example 2

Production of Soyasapogenol B by Strain PF1226

The seed medium of Example 1 (20 ml) dispensed into a 100-ml Erlenmeyer flask was sterilized at 120° C. for 15 minutes. One platinum loopful of slant agar culture of PF1226 strain (FERM BP-7476)was inoculated into the medium thus prepared and incubated at 25° C. for 2 days with shaking. Next, the production medium (100 ml) dispensed into a 500-ml Erlenmeyer flask was sterilized at 120° C. for 15 minutes, into which 2 ml of the culture thus obtained were inoculated and incubated at 25° C. for 4 days with shaking.

The resulting culture (300 ml) was extracted with ethyl acetate (300 ml) and the ethyl acetate layer was concentrated under reduced pressure to obtain an oily substance (700 mg). This substance was applied to a column of silica gel (Wako Gel C-300, a product of Wako Pure Chemicals; 70 g) and eluted with hexane-acetone (3:1). Fractions each containing a single substance were collected and concentrated to dryness to obtain soyasapogenol B (120 mg) and soyasapogenol A (6 mg).

Thin layer chromatography (TLC:MERCK 1.05715.; development system: hexane-acetone (2:1))

Soyasapogenol B: Rf 0.38
Soyasapogenol A: Rf 0.28

Identification of Soyasapogenol B

Physicochemical characteristics and various spectral data of soyasapogenol B obtained in Example 1 and Example 2 were identical with those of the standard soyasapogenol B. Soyasapogenol B obtained in the present invention gives the following $^{13}C$ NMR data (chemical shift (ppm),multiplicity and assignment, in order). 38.4 (t, C-1), 27.6 (t, C-2), 80.8 (d, C-3), 42.7 (s, C-4), 55.8 (d, C-5), 18.4 (t, C-6), 33.1 (t, C-7), 39.7 (s, C-8), 47.7 (d, C-9), 36.6 (s, C-10), 23.7 (t, C-11), 122.3 (d, C-12), 143.9 (s, C-13), 42.0 (s, C-14), 25.9(t, C-15), 28.2 (t, C-16), 37.4 (s, C-17), 44.7 (d, C-18), 46.1 (t, C-19), 30.5 (s, C-20), 41.4 (t, C-21), 76.6 (d, C-22), 22.4 (q, C-23), 64.5(t, C-24), 16.1 (q, C-25), 16.8 (q, C-26), 25.4 (q, C-27), 20.0 (q, C-28), 32.8 (q, C-29), 28.2 (q, C-30)

The numbering used for the assignment is shown in the following chemical formula.

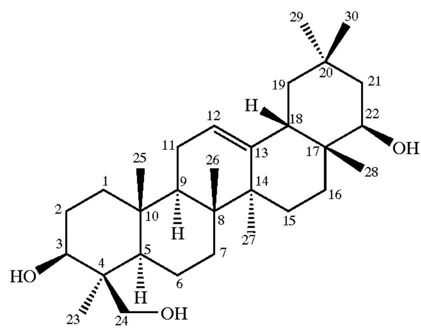

What is claimed is:

1. A method of producing soyasapogenol B comprising the steps of culturing microorganisms that belong to genus *Neocosmospora* and convert a glycoside having soyasapogenol B as an aglycone to soyasapogenol B, in a medium containing a glycoside having soyasapogenol B as an aglycone, and then collecting soyasapogenol B from the resulting culture.

2. A method of producing soyasapogenol B comprising the steps of culturing microorganisms that belong to genus *Eupenicillium* and convert a glycoside having soyasapogenol B as an aglycone to soyasapogenol B, in a medium containing a glycoside having soyasapogenol B as an aglycone, and then collecting soyasapogenol B from the resulting culture.

3. A method according to claim 1 wherein, the microorganism which belongs to genus *Neocosmospora* is *Neocosmospora vasinfecta* var. *vasinfecta.*

4. A method according to claim 2 wherein, the microorganism which belongs to genus *Eupenicillium* is *Eupenicillium brefeldianum.*

5. A method according to claim 1 wherein, the microorganism which belongs to genus *Neocosmospora* is *Neocosmospora vasinfecta* var. *vasinfecta* PF1225 (FERM BP-7475).

6. A method according to claim 2 wherein, the microorganism which belongs to genus *Eupenicillium* is *Eupenicillium brefeldianum* PF1226 (FERM BP-7476).

7. A method of producing soyasapogenol B comprising the steps of bringing a glycoside having soyasapogenol B as an aglycone into contact with a culture which is obtained by culturing microorganisms that belong to genus *Neocosmospora* and convert a glycoside having soyasapogenol B as an aglycone to soyasapogenol B, and then collecting soyasapogenol B from the resulting culture.

8. A method of producing soyasapogenol B comprising the steps of bringing a glycoside having soyasapogenol B as an aglycone into contact with a culture which is obtained by culturing microorganisms that belong to genus *Eupenicillium* and convert a glycoside having soyasapogenol B as an aglycone to soyasapogenol B, and then collecting soyasapogenol B from the resulting culture.

9. A method according to claim 7 wherein, the microorganism which belongs to genus *Neocosmospora* is *Neocosmospora vasinfecta* var. *vasinfecta.*

10. A method according to claim 8 wherein, the microorganism which belongs to genus *Eupenicillium* is *Eupenicillium brefeldianum.*

11. A method according to claim 7 wherein, the microorganism which belongs to genus *Neocosmospora* is *Neocosmospora vasinfecta* var. *vasinfecta* PF1225 (FERM BP-7475).

12. A method according to claim 8 wherein, the microorganism which belongs to genus *Eupenicillium* is *Eupenicillium brefeldianum* PF1226 (FERM BP-7476).

13. An isolated biologically pure strain, PF1225 deposited at the National Institute of Bioscience and Human-Technology, the National Institute of Advanced Industrial Science and Technology, under the accession number FERM BP-7475, and mutants thereof.

14. An isolated biologically pure strain, PF1226 deposited at the National Institute of Bioscience and Human-Technology, the National Institute of Advanced Industrial Science and Technology, under the accession number FERM BP-7476, and mutants thereof.

* * * * *